United States Patent [19]
Rosenschein

[11] Patent Number: 5,836,896
[45] Date of Patent: Nov. 17, 1998

[54] METHOD OF INHIBITING RESTENOSIS BY APPLYING ULTRASONIC ENERGY

[75] Inventor: Uri Rosenschein, Kfar Daniel, Israel

[73] Assignee: Angiosonics, Morrisville, N.C.

[21] Appl. No.: 700,064

[22] Filed: Aug. 19, 1996

[51] Int. Cl.$^6$ .................................................. A61B 17/22
[52] U.S. Cl. .................................................................... 601/2
[58] Field of Search .............................. 601/2–4; 607/97; 606/159, 1; 604/22; 128/898

[56] References Cited

U.S. PATENT DOCUMENTS

| | | | |
|---|---|---|---|
| 5,163,421 | 11/1992 | Bernstein et al. | 606/159 X |
| 5,213,561 | 5/1993 | Weinstein et al. | 600/7 |
| 5,269,291 | 12/1993 | Carter | 128/24 AA |
| 5,344,395 | 9/1994 | Whalen et al. | 604/22 |
| 5,474,531 | 12/1995 | Carter | 604/22 |
| 5,527,337 | 6/1996 | Stack et al. | 606/198 |
| 5,599,844 | 2/1997 | Grainger et al. | 514/651 |

*Primary Examiner*—Francis Jaworski
*Attorney, Agent, or Firm*—Stroock & Stroock & Lavan LLP

[57] ABSTRACT

A method and system for inhibiting restenosis by compromising the migration, viability and adhesion of mammalian smooth muscle cells (SMC) is disclosed. The method comprises irradiating the SMC with ultrasonic energy, in an amount which has been found to be effective in inhibiting the migration and adherence of SMC. This method is especially useful in the prevention of restenosis in a blood vessel of a mammal associated with the migration of SMC in the blood vessel following vascular intervention, such as angioplasty. The system disclosed for the prevention of restenosis in a blood vessel of a mammal associated with the migration of SMC in the blood vessel following vascular intervention includes an ultrasonic energy source; a transmitter for transmitting the ultrasonic energy to the blood vessel; and a control unit.

16 Claims, 8 Drawing Sheets

METHOD OF INHIBITING RESTENOSIS BY APPLYING ULTRASONIC ENERGY

FIELD OF THE INVENTION

The present invention relates generally to a method for inhibiting restenosis in mammals by compromising the migration, viability and/or adherence of smooth muscle cells within a mammalian blood vessel. In particular, the method of the invention is useful in the prevention of restenosis following angioplasty or other invasive cardiovascular therapies.

BACKGROUND OF THE INVENTION

Coronary artery disease is a major cause of morbidity and mortality in the Western world. The disease is typically manifested in intravascular stenosis (narrowing) or occlusion (blockage) due to atherosclerotic plaque. Percutaneous transluminal coronary balloon angioplasty (PTCA) is widely used as the primary treatment for arteriosclerosis involving stenosis.

Unfortunately, a significant fraction of the patients who have undergone coronary balloon angioplasty develop restenosis at the treated site within 3–6 months after the procedure. Austin G. E., Ratliff M. B., and Holman J. suggest that intimal proliferation of smooth muscle cells may account for the observed recurrent coronary artery stenosis after percutaneous transluminal coronary angioplasty in "J. Am. Coll. Cardiol." (1985) 6:369–375.

The limitations of balloon angioplasty stimulated an explosion of new angioplasty techniques, including laser, stents, thermal, and arthrectomy devices. However, these new devices also suffer from the same serious drawback of the previous method of treatment, primarily due to their inability to damage the atherosclerotic lesion without incurring injury to the arterial wall. The resulting injury repair process, which includes migration of smooth muscle cells to the cite of the injury, then leads to restenosis.

Thus, restenosis following successful balloon angioplasty or other new intervention techniques, remains a major problem limiting the long term efficacy of angioplasty procedures. In up to 50% of treated patients, a clinically significant restenosis develops.

Ultrasound angioplasty is a relatively new transcatheter technology developed for arterial recanalization and is described, for example, in U.S. Pat. No. 4,870,953 to DonMicheal et al. In this method, generally, the clots in the coronary arteries are lysed by application of high-power, low-frequency ultrasound (ULS) delivered by a dedicated device. Studies have suggested that ultrasound energy at levels known to induce effective thrombus lysis appear to be minimally harmful to a blood vessel wall. For example, the ultrasound power level required to ablate thrombi is about $\frac{1}{40}$ of that required to induce arterial wall damage. Rosenschein U., Bernstein J. J., DiSegni E., Kaplinsky E., Bernheim J., and Rozenszsajn L. describe experimental procedures and results of ultrasonic angioplasty leading to disruption of atherosclerotic plaques and thrombi and arterial recanalization in "J. Am. Coll. Cardiol." (1990) 15:711–717. The selective ablation of thrombi by ultrasound makes this technology a potentially effective and safe clinical method to treat patients with coronary thrombosis, including heart attacks.

All vascular interventional techniques (e.g. PTCA, stents, lasers) are associated with intimal and medial damage of the treated blood vessel which leads to platelet adhesion, aggregation and the release of an array of mitogens. The mitogens stimulate migration of smooth muscle cells (SMC) from the media to the intima and across the internal elastic lamina, followed by their proliferation, extracellular matrix production, neointima formation and the resulting restenosis of the treated artery.

Thus, vascular injuries induce the synthesis of multiple factors which induce SMC migration and proliferation leading to neointimal formation which is manifested clinically and angiographically as restenosis. Ross R. describes this pathogenesis of atherosclerosis in "Nature" (1993) 362:801–809. The effect of therapeutic ultrasound on SMC functions (primarily migration, adhesion and proliferation or viability) which play a role in the restenotic process has generally not as yet been researched excepting the work done by applicant herein.

To date, the strategies to treat restenosis were targeted mainly at inhibiting SMC proliferation or viability. For example, WO 94/07529 describes the use of a vascular smooth muscle binding protein which binds in a specific manner to the cell membrane of a vascular SMC thus inhibiting the activity of the cell. U.S. Pat. No. 5,472,985 issued to Grainger, describes the use of TGF-beta activators and production stimulators to inhibit the pathological proliferation of vascular SMC. All these strategies have failed to date to demonstrate clinical efficacy in preventing restenosis. Due to the high incidence of restenosis after non-surgical recanalization of occluded and stenotic arteries, an effective method to prevent this complication can be expected to rapidly find wide application.

Fahnestock M., Rimier U. G., Yamakawi R. M., Ross P., and Edmonds P. D. studied the effect of in vitro ultrasound exposure on neuroblastoma cell membrane. As reported in "Ultrasound Med. Biol." (1989) 15:133–144, they found that high frequency ultrasound on cell lines affects cell permeability which is dependent on the integrity of the cell membrane. After low frequency ultrasound treatment, a transient decrease in cell proliferation of cancer cells, without significant changes in cell cycle distribution and cell alteration of intracellular adhesion, has also been observed by Nicolai H., Steinbach P., Knuechel-Clarke R., Grimm D., Roessler W., Wieland and Hofstaedter W. F. They report that proliferation of tumor spheroids may be reduced after shockwave treatment in "J. Cancer Res. Clin. Oncol." (1994) 120:438–441.

In a presentation at the 1995 Conference of the European Society of Cardiology (Amsterdam, August 20–24), the applicant demonstrated that ultrasound induces inhibition of SMC migration and adhesion. No mention was made of the effect of ultrasound on restenosis however. The applicant has also described portions of the invention herein in U. Rosenschein, A. Alter and L. A. Rozenszajn, in *Endoluminal Stenting*, (Sigwart, U., Ed.) W. B. Saunders Co. Ltd. (1996) pgs. 129–133.

Until now, therapeutic ultrasound has been used mainly for recanalized arteries occluded by clots. None of the modalities currently employed for arterial recanalization is used to modify SMC biology and prevent restenosis.

SUMMARY OF THE INVENTION

Generally speaking, in accordance with the invention, a method of inhibiting restenosis by applying ultrasonic energy is provided which inhibits the migration, viability and adherence of smooth muscle cells in a blood vessel. The method includes irradiating smooth muscle cells with ultrasonic energy in an amount effective for compromising the migration, viability or adhesion of the smooth muscle cells.

Also provided in accordance with the invention, is a therapeutic method for the prevention of restenosis associated with smooth muscle cell migration, viability and adherence in a blood vessel following vascular intervention, which includes exposing the smooth muscle cells in the blood vessel to ultrasonic energy in an amount which compromises the migration, viability and/or adhesion of the smooth muscle cells.

In accordance with the invention, a system for the prevention of restenosis in a blood vessel following vascular intervention is also provided, which includes an ultrasonic energy source coupled to a transmitter which transmits the ultrasonic energy to a blood vessel, and a control unit which controls the amount of ultrasonic energy transmitted to the blood vessel to an effective amount for compromising the migration, viability and adherence of smooth muscle cells contained in the blood vessel.

The present invention is based on the surprising and unexpected discovery that ULS irradiation is effective in inhibiting the migration, viability and/or adherence of SMC.

It is therefor an object of the present invention to provide a method for inhibiting SMC migration, viability and adherence.

It is another object of the present invention to provide a therapeutic method for preventing restenosis of a blood vessel following angioplasty.

It is a further object of the present invention to provide a system which can be used to prevent restenosis following intervention in coronary disease patients.

According to an additional aspect of the present invention, there is provided a method for inhibiting the migration, viability and adhesion of mammalian smooth muscle cells (SMC) which includes irradiating the SMC with a restenosis inhibiting amount of ultrasonic energy.

In a preferred embodiment of the present invention, the ultrasonic energy has a power at least above the cavitation threshold of water.

According to yet another aspect of the present invention, there is provided a therapeutic method for the prevention of restenosis in a blood vessel of a mammal associated with the migration of SMC in the blood vessel following vascular intervention which includes exposing the blood vessel to ultrasonic energy to inhibit the migration, viability and/or adhesion of the SMC therein and prevent restenosis.

According to still another aspect of the present invention, there is provided a system for the prevention of restenosis in a blood vessel of a mammal associated with the migration, viability and/or adhesion of SMC in the blood vessel following vascular intervention including an ultrasonic energy source, and a transmitter for transmitting the ultrasonic energy to the blood vessel. The system preferably also includes instructions for using the ULS energy source and transmitter in performing a disclosed method of the invention.

Still other objects and advantages of the invention will in part be obvious and will in part be apparent from the specifications and drawings.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

The present invention will be better understood with reference to the following detailed description taken in connection with the accompanying drawings, in which:

FIG. 5a shows an unsonicated cell. FIGS. 5b and 5c show SMC after exposure to ultrasound;

FIG. 6a shows the cytoskeletal organization of SMC with the uninterrupted α-actin filaments; FIG. 6b shows the SMC 0.2 hours after ultrasound; and FIG. 6c shows the SMC 24 hours after ultrasound;

DETAILED DESCRIPTION OF PREFERRED EMBODIMENTS

Figure 1:
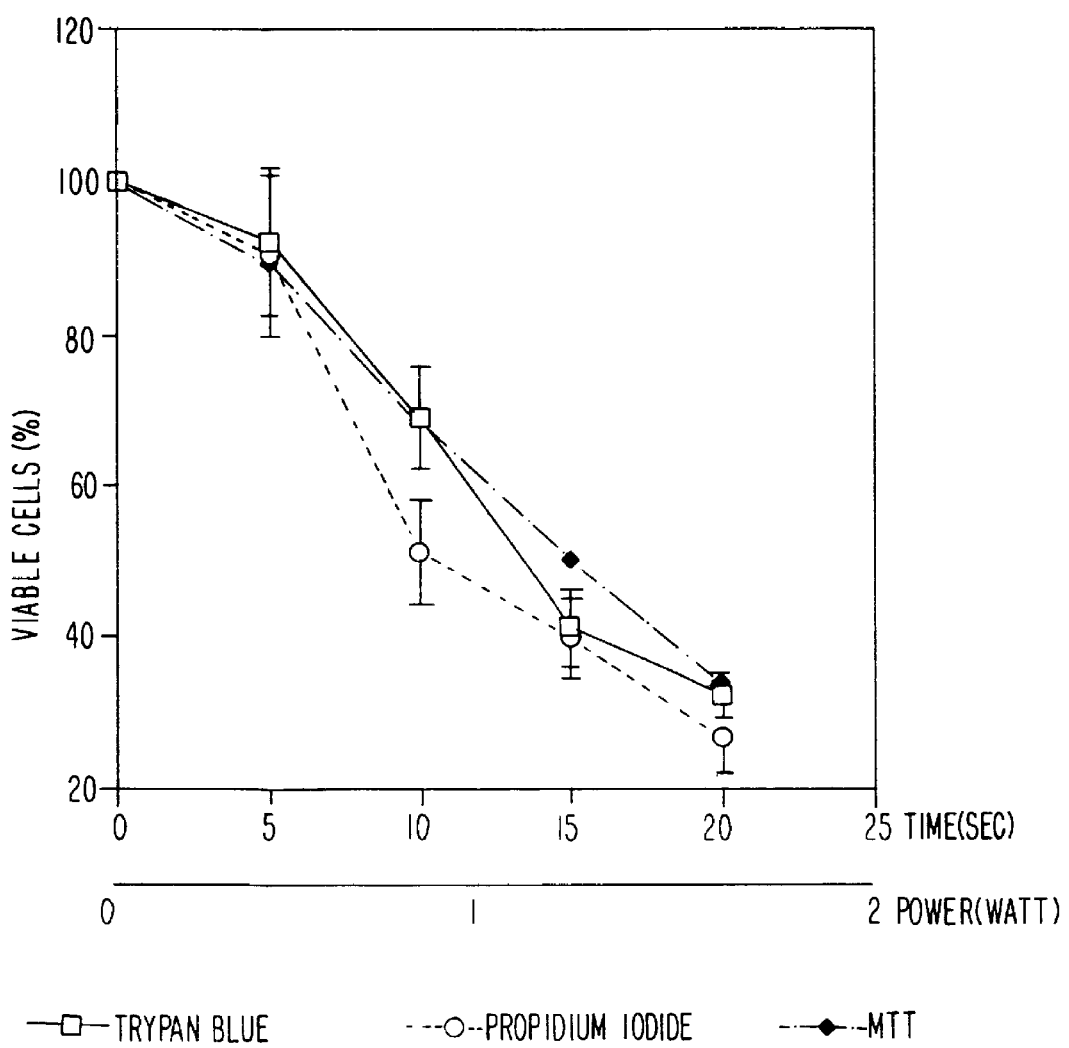
FIG. 1 is a graph illustrating the viability of SMC as a function of exposure to ultrasound (ultrasound power×time of sonication) at a frequency of 20 kHz.

Vascular smooth muscle cells (SMC) play a fundamental role in atherosclerotic legion formation and restenosis. Vascular injury induces synthesis of multiple factors, and mitogens, which ultimately induce SMC migration, adhesion and/or proliferation (viability) leading to intimal hyerplasia. For example, a significant fraction of patients ( up to 50%) who have undergone coronary balloon angioplasty develop restenosis. Restenosis is due primarily to the vascular injury induced by percutaneous ballon angioplasty which leads to migration and adherence of SMC in to the intima of the blood vessel, followed by excessive proliferation and formation of neo-intimal clusters.

The applicant has studied the effects of therapeutic ultrasound on the migration, viability and adherence functions of smooth muscle cells, which play a role in the restenotic process. Therefore, the applicant has studied the structural and functional changes associated with the application of ultrasound on smooth muscle cells. Initially, in vitro testing was done to determine the parameters and results of ultrasound radiation of smooth muscle cells.

Bovine aortic SMC (BASMC) were prepared by the explant technique and cultured on 100×20 mm tissue culture dishes (Falcon, Oxanard, Calif.) in Dulbecco-modified Eagle's medium (DMEM) supplemented with 10% heat-inactivated calf serum (CS) (5% fetal calf serum and 5% newborn calf serum), L-glutamine (0.3 mg/ml), penicillin 100 (μg/ml), streptomycin (100 μg/ml) and amphotericin (0.25 μg/ml) (Biological Industries, Beit Haemek, Israel). For experiments, cells at passage levels 9 to 17 were replicate-plated into 100 mm culture dishes, refed every third day and used at confluence. All cell growth was conducted at 37° C. in a fully humidified incubator containing 10% $CO_2$ in air.

Cultures were passaged immediately before fall confluence by brief exposure to PBS containing trypsin (0.5 mg/ml) and ethylene-diamine-tetraacetic acid (EDTA) (0.5 mmoles/L) at 37° C. and grown to confluence in DMEM containing 10% CS. Cell growth was observed under an inverted phase contrast microscope (Carl Zeiss Oberkochen, Germany) with a magnification of 200x. The cells were characterized as SMC by morphologic criteria as well as by expression of smooth muscle α-actin in accordance with the procedure of Powell R. J., Cronenwett J. L., Filliner M. F., and Wagner R. J., as outlined in their study on the effect of endothelial cells and transforming growth factor-B1 on cultured vascular smooth muscle cell growth patterns in "J. Vasc. Surg." (1994) 20:787–94.

SMC of confluent cultures were trypsinized, and thereafter were suspended, $2.5 \times 10^6$/5 ml DMEM, in a 16×125 mm culture tube (Corning-Staffordshire, UK). They were then exposed to ULS using a sonicator (Vibra Cell, Sonic Materials Inc., Danbury, Conn.). The sonicator consists of a resonant length (90 mm) of a vertically suspended, thin titanium probe (diameter 2 mm), which resonates at a frequency of 20 kHz and variable power levels. To prevent aerosol formation during sonication, the depth of immersion of the probe is adjusted so that the meniscus of the liquid comes in contact with the ultrasonic wire at a displacement node.

Each of the following experiments were done in triplicate and repeated at least 4 times. Data is typically expressed as mean ±SD. The student's t-test was used in all experiments. For the experiments on adherence, analysis of variance was also performed. A p value $\leq 0.05$ was considered to be significant.

Viability Experiment

The viability of sonicated SMC was tested by propidium iodide (PI) staining, trypan blue exclusion and tetrazolium (MTT) methods. In the PI staining method, SMC ($1 \times 10^6$) were suspended in PBS containing sodium azide (0.3 mg/ml) and PI (0.5 μg/ml) (Sigma, St. Louis, Mo.). The cells were analyzed for viability within 30 minutes after adding the PI solution using an Epics-Profile II flow cytometer (Coulter Corp., Luton, UK) measuring red fluorescence with band pass filters >650 mn.

In the MTT assay, aliquots of SMC (100 μL) were transferred to flat-bottomed 96 microwell plates. MTT (Sigma, St. Louis, Mo.) was dissolved in DMSO (Sigma, St. Louis, Mo.) and diluted with PBS to a final concentration of 5 mg/ml; 10 μL MTT were added to each well. The plates were incubated at 37° C. for 2 hours and 100 μL of 0.04N HCl in isopropanol were added to each well. The viability of cells was evaluated in an ELISA reader (Kontron SLT-210) using a 550 nm filter.

In the trypan blue exclusion assay, aliquots of SMC were removed and the dye (0.4% in PBS) was added to the cell suspension. The extent of dye uptake being indicative of cell damage, viable cells were counted using a hemocytometer.

Each experiment was performed with a given number of unseparated viable cells after sonication. The same number of unsonicated cells was used as controls.

Referring to FIG. 1, it can be seen that excellent correlation between ultrasound dose (ultrasound power×time of sonication) and SMC viability was observed using the PI (r=0.98649), MTT (r=0.9890) and trypan blue (r=0.98582) methods over a range of sonication times (1–20 sec) and power (0–2 watts). The LD50 of the ULS was established as sonication of 1.5 watts for 15 sec. at a frequency of 20 kHz and was used in all experiments.

Migration Experiment

The migration capacity of the sonicated BASMC was assayed in a 48-well microchemotaxis chamber (Neuro Probe, Inc., Cabin John, Md.). Subconfluent SMC were detached from 100 mm culture dishes by incubation with trypsin-EDTA. To avoid excessive exposure to trypsin, the incubation time was usually restricted to 3 minutes. The cells were washed once in DMEM, resuspended in DMEM-0.5% CS and then sonicated. The number of sonicated SMC was adjusted to $10^6$ viable cells/ml in DMEM-0.5% CS.

In the migration assay, the bottom wells contained DMEM supplemented with either 0.5% CS or 10% CS, which acted as chemoattractant. Fifty μL of the sonicated SMC samples were placed in the upper wells of the chamber. A 5 μm pore size polyvinyl pyrolidone-free polycarbonate filter membrane (Neuro Probe, Inc.) was placed above the lower wells. The chamber was assembled and incubated at 37° C. in a humidified atmosphere of 10% $CO_2$ in air for 90 minutes. The filter was then removed and the vital SMC that had migrated through the filter membrane were stained with May-Grunwald Giemsa (Sigma, St. Louis, Mo.). The filter was then mounted on a glass slide. Cells that had migrated across the filter were counted using a light microscope with a micrometered eye piece (Carl Zeiss, Oberkochen, Germany) and a magnification of 320x.

The migration ability was tested 0.2 hours, 2 hours and 24 hours after sonication and expressed as the average number of migrating SMC/field, counted in 9 fields, in triplicate wells. Non-sonicated SMC served as controls. All the p values were computed relative to the control.

Figure 2A:
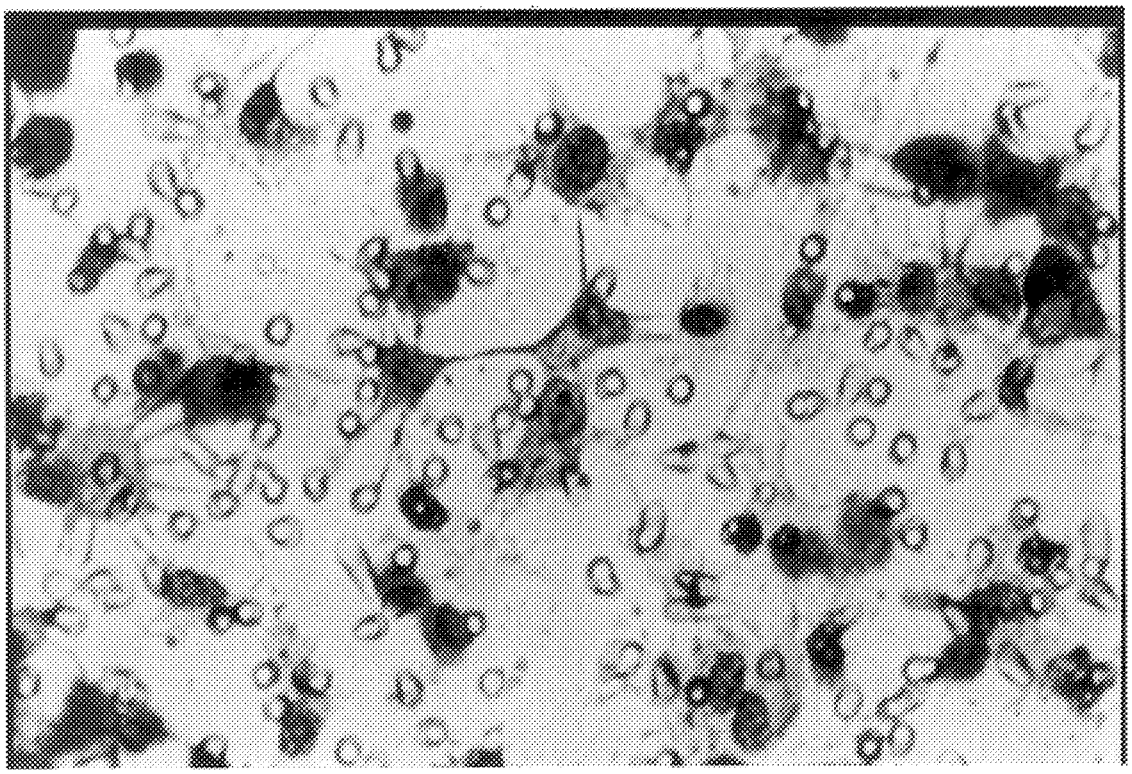
FIGS. 2a and 2b are representative, light microscope views of SMC that migrated through the 0.5 µm pore filter membrane of the chamber before (FIG. 2a) and after (FIG. 2b) exposure to ultrasound. The stain is May-Grunwald Giemsa.
Figure 2B:
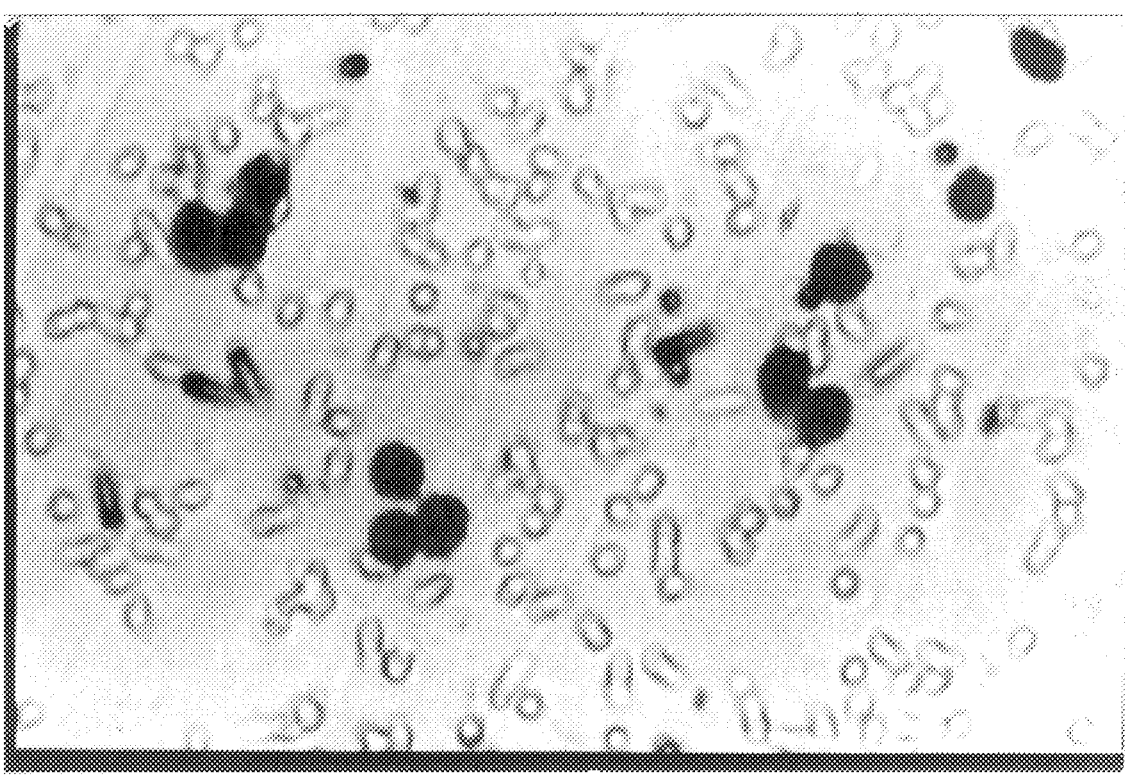

Examination under a light microscope of non-sonicated SMC that had migrated across the filter membrane revealed that the cell had a flattened shape and that its membrane exhibited the prominent lamellipodia characteristic of migrating cells. The unsonicated SMC migrated across the filter membrane in large numbers (FIG. 2a). Sonicated SMC had lesser asymmetry in the architecture of their membrane. Few cells were able to cross the filter membrane and those that did were round in shape with very small lamellipodia (FIG. 2b).

Figure 3:
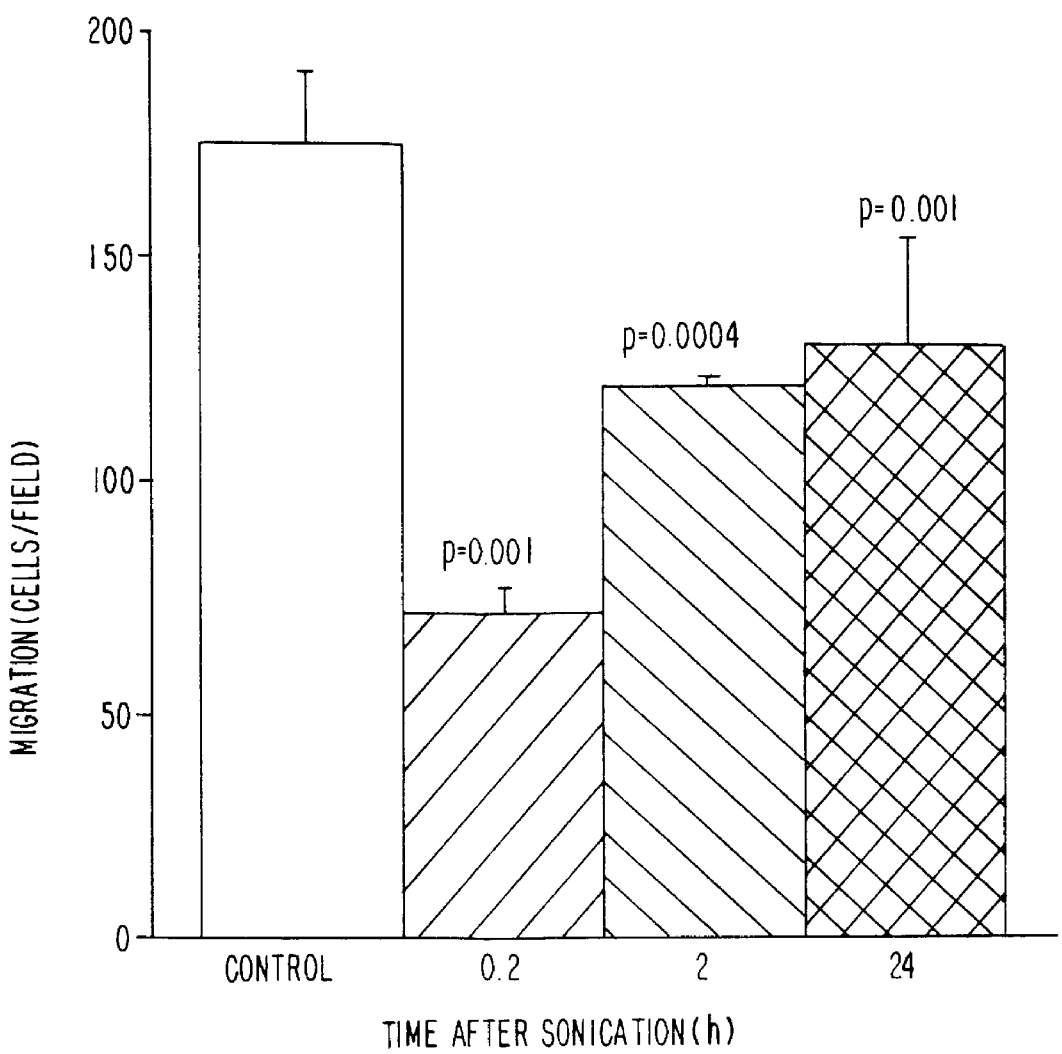
FIG. 3 is a bar graph illustrating the migration capacity of sonicated SMC evaluated by their ability to cross a filter membrane.

The migration capacity of sonicated SMC was reduced both with or without the use of chemoattractant (10% CS) (FIG. 3). Twelve minutes after SMC were exposed to ultrasound, in the presence of chemoattractant, their motility decreased 2.4 fold (72±5 vs. 175±16 cells/field, p=0.0001).

Two hours after exposure to ultrasound, the inhibition of cell motility decreased partially, to a 1.3 fold reduction in migration (121±2 vs. 175±16 cells/field, p=0.0004). Cell migration remained significantly diminished 24 hours after ultrasound (130±24 vs. 175±16, p=0.001).

Adhesion Experiment

The assay for SMC adherence capacity was a modification of the method described by Dartsch P. C., Voisard R., Bauriedel G., Hofling B., and Betz E. in a study on characteristics and cytoskeletal organization of cultured smooth muscle cells from human primary stenosing and restenosing in lesion, reported in "Arteriosclerosis" (1990) 10:62–75. After sonication, viable SMC were centrifuged at 200 g for 10 minutes. The pelleted cells were suspended in Waymouth, HB 752/1 and Ham's F-12 medium (2:1, v/v) and seeded in 0.2 ml aliquots of $5\times10^4$ cells/ml in flat-bottomed, 96 microwell plates (Nunc, Denmark) either untreated or precoated with fibronectin (25 ng/mm$^2$) (Biological Industries, Beit Haemek, Israel). The SMC were incubated at 37° C. and the adherence capacity of the SMC was analyzed frequently during the first 3 hours after sonication. The adherence capacity was further followed once every 24 hours for 5 days. At each data collection point along the time axis, the supernatant was discarded and the non-adherent cells removed by gently washing the wells twice with PBS. The adherent cells were counted using an inverted phase contrast microscope with a micrometered eye piece (Carl Zeiss, Oberkochen, Germany) and a magnification of 200x. The adherence capacity was expressed as the average number of adhering SMC/field, in 3 fields of triplicate wells. Non-sonicated SMC served as controls.

Figure 4A:
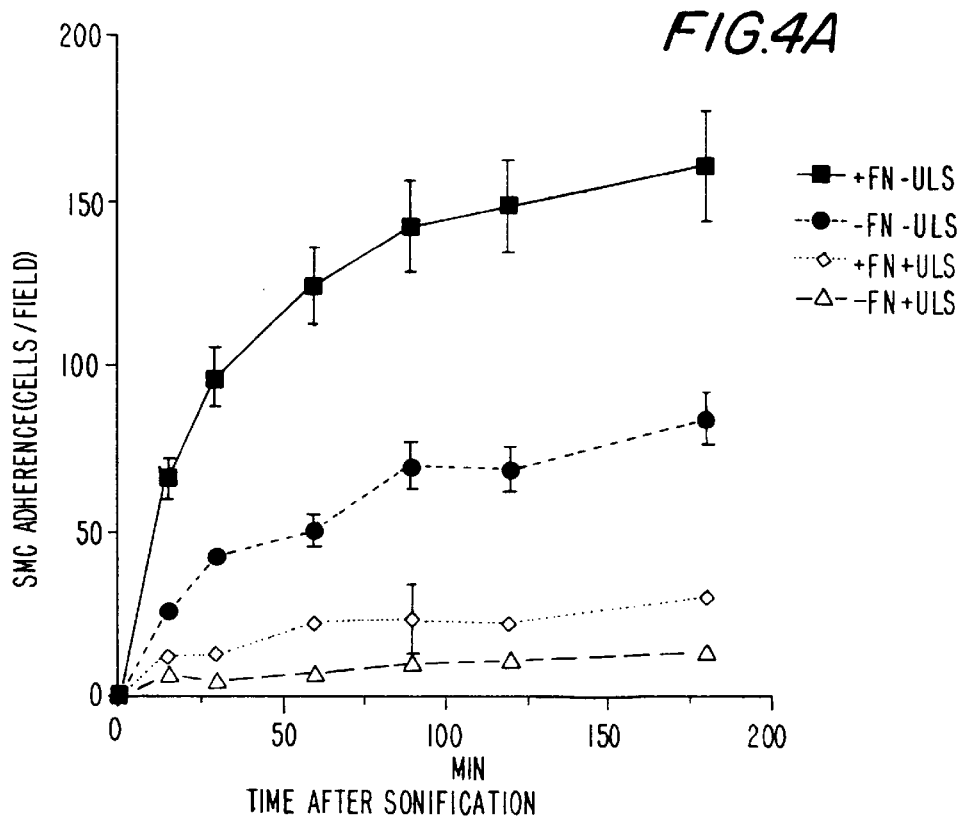
FIGS. 4a and 4b are graphs illustrating the time course of the change in adhesion capacity of sonicated SMC. The adherence capacity was quantified 6 times during the first 3 hours (FIG. 4A) and every 24 hours thereafter for 120 hours (FIG. 4B).
Figure 4B:
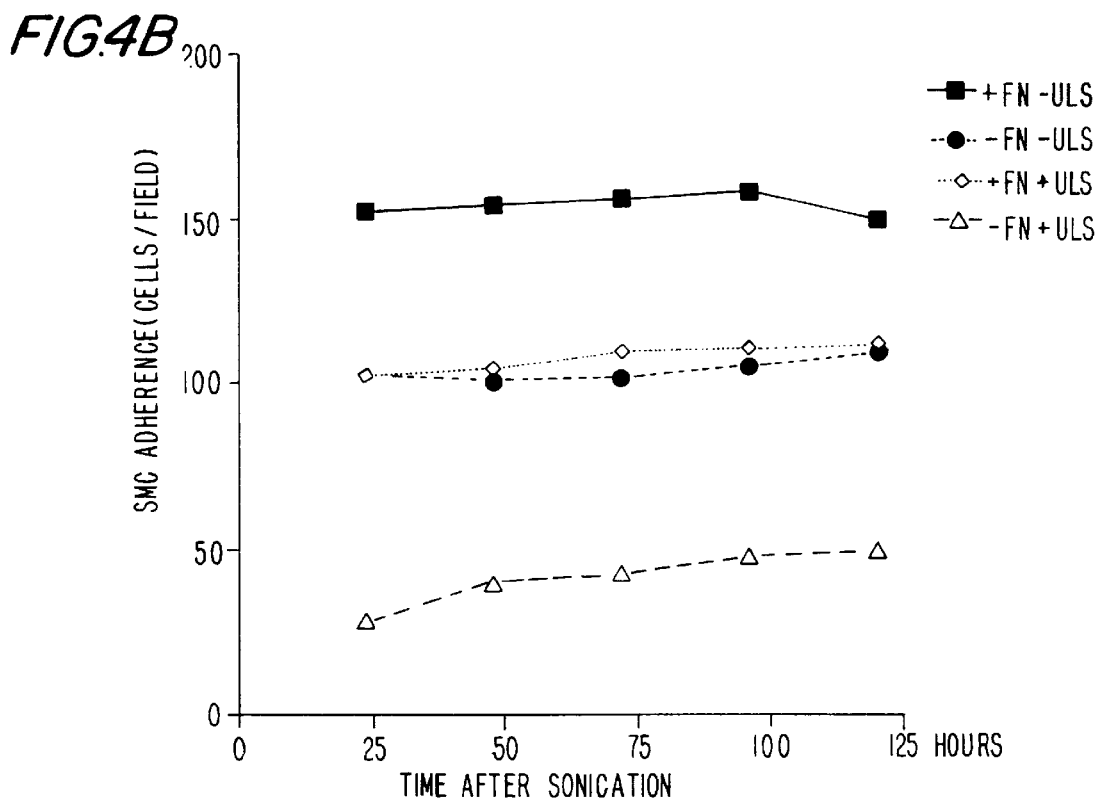

The adhesion of cultured SMC exposed to ultrasound was significantly reduced in all the assays performed after sonication (FIG. 4). When tested on fibronectin-coated surfaces, a 5.5 fold decrease was recorded 3 hours after sonication (29±3 vs. 160±20 cells/field, p=0.0001). On plastic surfaces, a 6.5 fold decrease (12.6±2.5 vs. 83±8 cell/field, p=0.0001) was noted. Analysis of variance shows that a significant decrease in adhesive capacity was attained (p=0.0001) at each time point, from 15 minutes to 180 minutes (FIG. 4A). The reduced adhesive capacity was evident for up to 120 hours after exposure to ultrasound (FIG. 4B).

Other Experiments

The incorporation of $^3$H-thymidine by sonicated SMC synchronized to the quiescent state (Go) by serum deprivation (0.5% CS), then stimulated to enter the cell cycle by serum repletion (10% CS), was measured and compared to non-sonicated cells.

SMC obtained from confluent cultures were cultured for 48 hours in the presence of 0.5% CS. The cells were well suspended 2.5×10$^4$/mL DMEM-0.5% CS, treated with ultrasound, and 12 minutes or 120 minutes after sonication, seeded in round-bottomed, 96 well microplates (Nunc, Denmark), 10$^5$ cells/well, in 0.2 ml medium containing either 0.5% or 10% CS and $^3$H-thymidine (3 $\mu$i/ml). After 2 hours, the cells were harvested onto filters by a cell harvester (Linca, Tel Aviv, Israel) and radioactivity determined by liquid scintillator spectroscopy (1600 TR, Packard, Conn.).

SMC obtained from confluent cultures were well suspended (2.5×10$^4$ mL), sonicated and seeded in flat-bottomed, 96 microwell plate (0.2 ml/well) in DMEM-10% CS and cultured at 37° C. in a humidified atmosphere of 10% CS in air for 48 hours. The culture medium was replaced by DMEM-0.5% CS for 48 hours and the SMC synchronized to the quiescent state. After 24 hours, $^3$H-thymidine (Nuclear Research Center, Negev, Israel) (3 uC/ml) was added for an additional 18 hours.

In a different experiment, the sonicated cells were seeded directly in DMEM-0.5% CS, cultured for 48 hours, and the procedure completed as described above.

The extent of $^3$H-thymidine incorporation was determined by aspirating the medium, subjecting the cultures to 10 washes with PBS, and extracting the $^3$H-thymidine in the cells with 0.2 ml of 0.2N NaOH/well. A volume of 0.1 ml of the extracted solution was added to 3 ml scintillation liquid/vial (Quicksafe, A. Zinsser, Germany) and the radioactivity counted in a liquid scintillation analyzer (1600 TR, Packard, Conn.).

$^3$H-thymidine incorporation, reflecting DNA synthesis, was expressed as the stimulation index. This index was defined as the ratio of the mean CPM of sonicated, stimulated (10% CS) SMC to the mean CPM of sonicated, non-stimulated (0.5% CS) cells. Non-sonicated SMC, activated or not activated by CS, served as controls.

In the short-term cultures, the SMC were in suspension during the entire incubation with $^3$H-thymidine. The proliferative capacities of SMC seeded for 12 minutes or for 120 minutes after sonication were similar to those of the unsonicated control cells. The stimulation indices were 3.2±0.7 vs. 3.29±0.7 p=NS and 3.19±0.5 vs. 3.25±0.5 p=NS, respectively.

In the long-term cultures, the 3H-thymidine was not significantly different whether the SMC were sonicated before initiation of culture with 10% CS or before the starvation step with 0.5% CS. The stimulation indices were 3.26±0.8 vs. 3.18±0.9 p=NS and 3.3±0.7 vs. 3.3±0.6 p=NS, respectively.

The data regarding DNA biosynthesis of SMC, as reflected by radioactive thymidine incorporation, indicate that the proliferative capacity of these cells was not significantly affected by sonication, whether the cells were stimulated or not.

The components of sonicated SMC cytoskeleton were examined by an immunofluorescent method. Actin fibers were examined by staining for $\alpha$-SM actin, intermediate filaments for vimentin, microtubules for tyrosinated alpha tubulin and focal contacts for vinculin. SMC were cultured at 37° C. in 10% $CO_2$ in air on a culture chamber slide (2×10$^3$ to 5×10$^3$ cells/10 mm$^2$) (Nunc, Denmark). Before full confluence, the cells were sonicated and the cytoskeletal components examined. Non-sonicated SMC served as controls under the same experimental conditions.

Cells were gently washed with PBS, then fixed with 3% paraformaldehyde for 10 minutes. The SMC were permeabilized with 0.5% triton-x100 in PBS for 2 minutes at room temperature, then washed 3 times with PBS, 5 minutes each time. The cells were subsequently incubated 60 minutes at room temperature with the first antibody, mouse anti-$\alpha$-smooth muscle actin (BioMakor, Rehovot, Israel), or mouse anti-vimentin, both diluted 1:100 with PBS, or mouse anti-vinculin (Immuno Sigma, St. Louis, Mo.), diluted 1:200, or anti-tyrosine tubulin (BioMakor, Rehovot, Israel) diluted 1:400.

After 3 washes with PBS, the cells were incubated with the fluorescein-conjugated second antibody, rat anti-mouse (Jackson, Immunoresearch Lab., Pa.) diluted 1:100 in PBS containing 1 mM $MgCl_2$ and 0.1 mM $CaCl_2$, and incubated for 30 minutes at room temperature. The cells were washed with PBS and the wall of the chamber slide removed. The slide was embedded in 90% glycerol, cover slips were mounted and sealed with nail polish. Structural changes in the cytoskeleton were examined using a fluorescent microscope (AH3-RFCA-Venox AHBT3, Olympus, Japan).

Phase-contrast microscopy (FIG. 5) showed that isolated SMC in suspension were rounded in shape. Within a few hours of attachment to the culture plates, either bare plastic or fibronectin-coated, they began to elongate and to assume an extended configuration. Later, they spread and assumed a flattened shape, resulting in increased cell size and surface area, until finally confluence, with the characteristic SMC growth pattern of hill and valley formation, was attained.

Figure 5A:
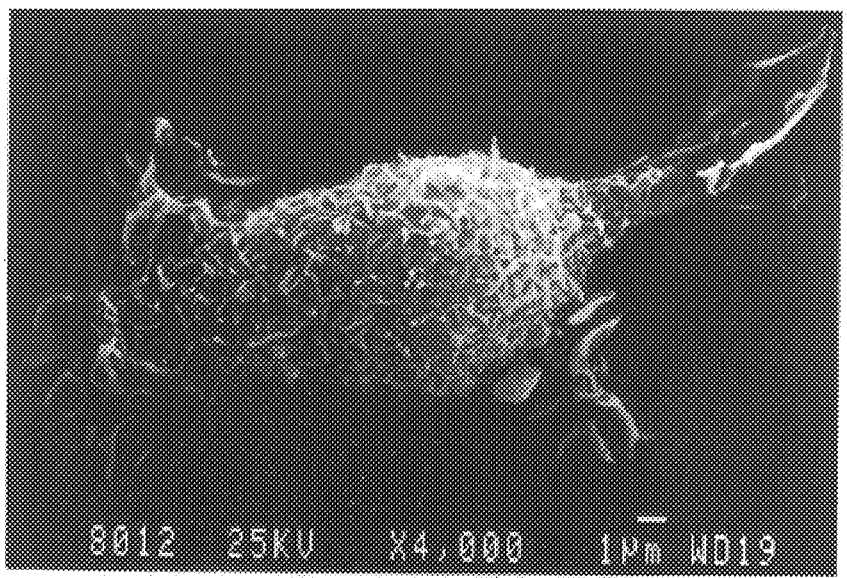
FIGS. 5a–5c are scanning electron microscope views of SMC morphology.
Figure 5B:
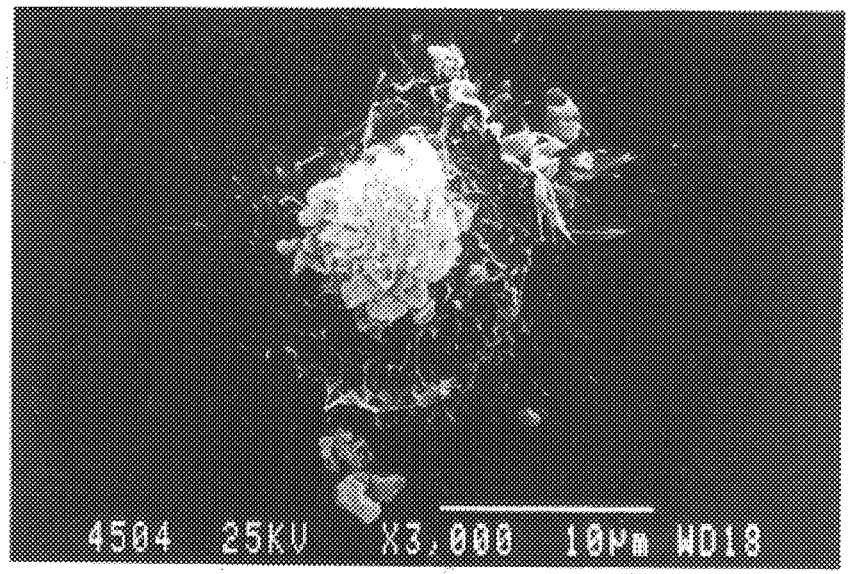
Figure 5C:
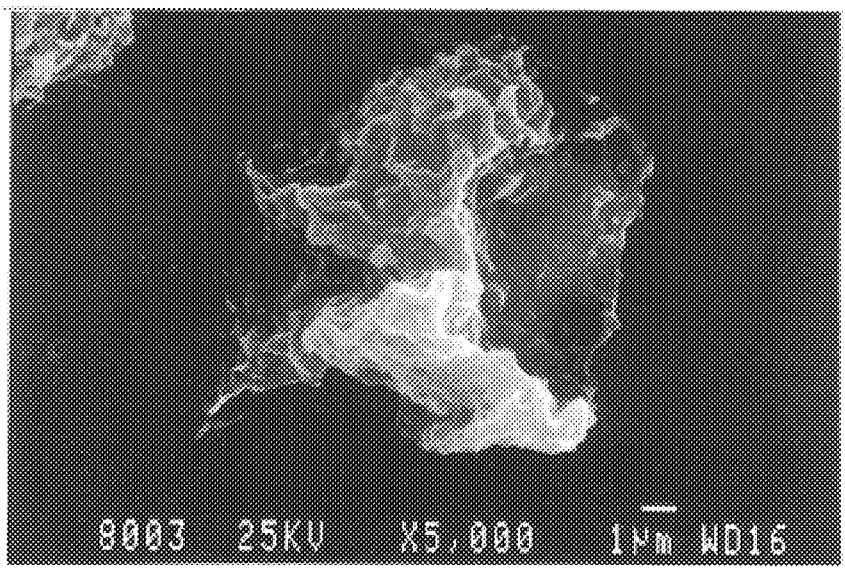

Microscopic examination of sonicated cells revealed changes in their morphology. Most of the cells were dispersed, the suspension consisted predominantly of single cells, some rounded in shape. Scanning electron microscopy showed that the surface of untreated cells was flat with lamellipodia and relatively thin, spike-like protuberances (FIG. 5a). After exposure to ultrasound, a change in cell morphology was noted: fewer cells exhibited lamellipodia (24% vs. 44% cells), zeiotic crowns appeared (FIG. 5b), large areas of membrane collapse were observed in 36% of the sonicated SMC (FIG. 5c), and extensive bleb formation was observed on the surface of the sonicated cells.

Figure 6A:
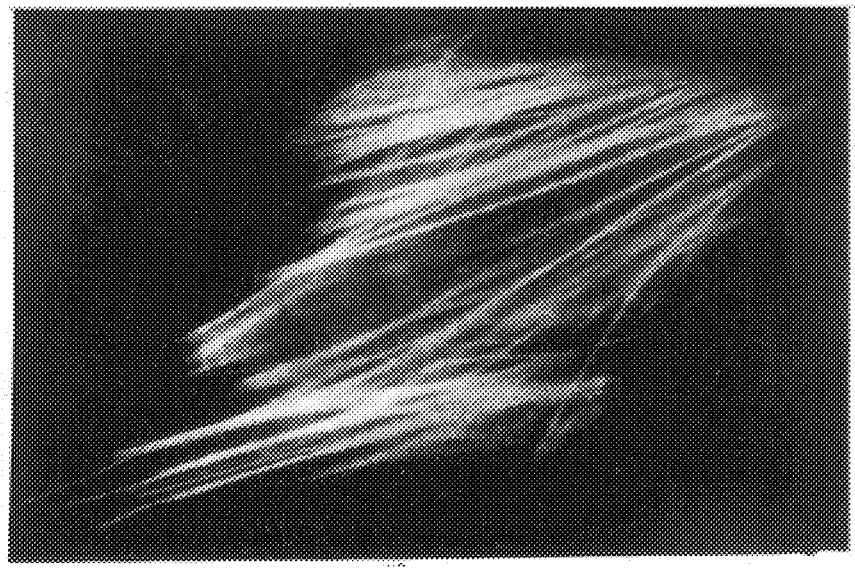
FIGS. 6a–6c show actin filaments of SMC which were stained using antibodies against α-SM actin and examined by indirect immunofluorescence technique.
Figure 6B:
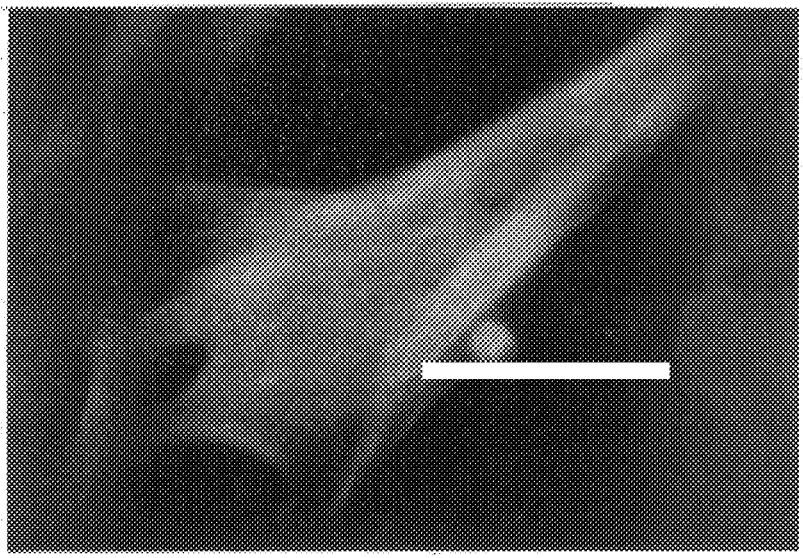
Figure 6C:
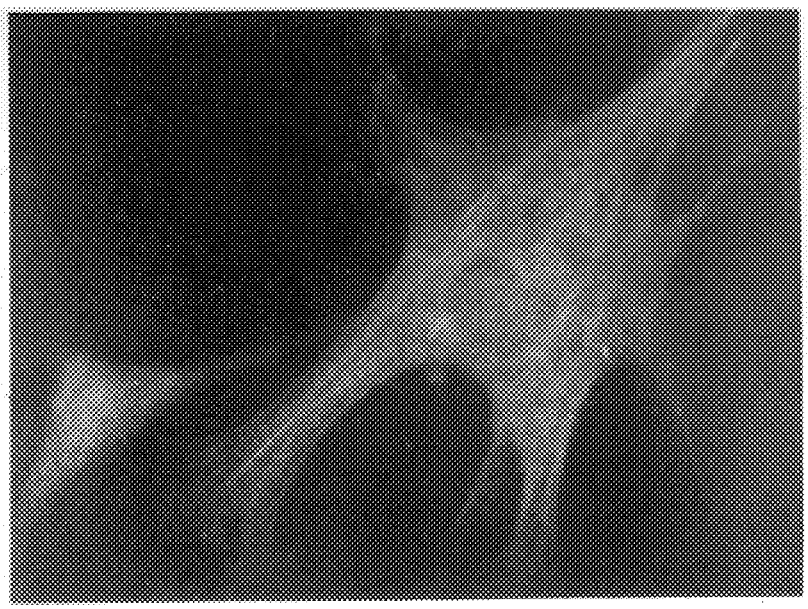

FIGS. 6a–c show the actin fibers which were examined by an immunofluorescence technique. The effect of sonication was manifested by rapid alteration of the normally well-organized, long, linear arrangement of the actin fibers (FIG. 6a). The intensity of stain of the stress fibers decreased with the simultaneous appearance of diffuse cytoplasmic fluorescence (FIG. 6b). After 24 hours in culture, partial reorganization of actin fibers could be detected in the sonicated SMC (FIG. 6c). However, residual cytoplasmic fluorescence suggested the presence of non-assembled actin. Distribution of focal contacts in the sonicated cells was also altered: vinculin concentration decreased in most cells as reflected by diminished stain intensity and the absence of the discrete characteristic punctate pattern at the termini of actin fibers at the periphery of the cells.

Figure 7A:
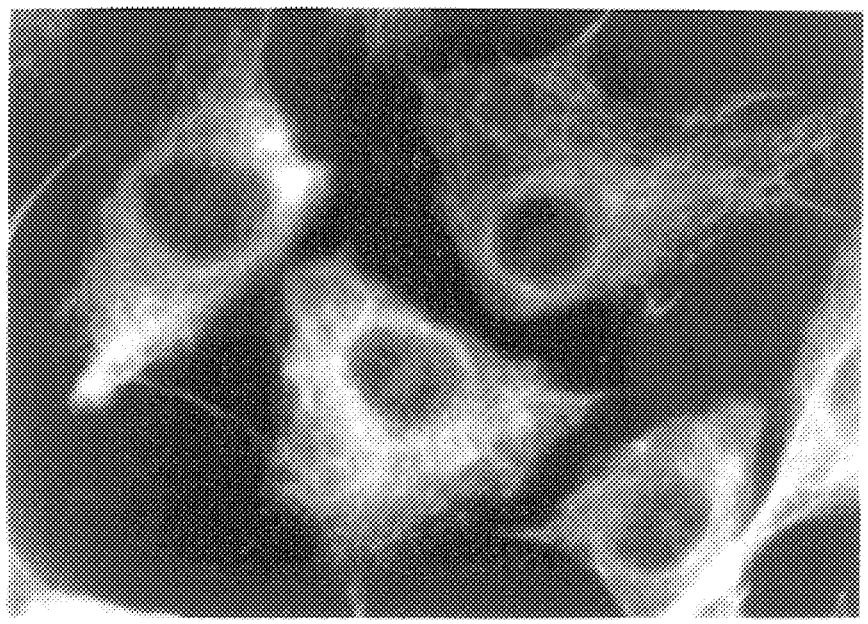
FIGS. 7a and 7b are photomicrographs of SMC after ULS which were stained with anti-tyrosine tubulin (FIG. 7a) or anti-vimentin (FIG. 7b) and examined by indirect immunofluorescence technique.
Figure 7B:

FIGS. 7a and 7b indicate no alteration of intermediate filaments and microtubule organization after sonication. Vimentin and tyrosine tubulin were organized in a filamentous, well-defined network originating in the nucleus, spreading throughout the cytoplasm and terminating near the periphery of the cell.

To evaluate signal transduction in sonicated SMC, the applicant investigated the α-adrenergic receptor phospholipase-C (PLC) pathway by triggering the α-adrenergic receptor with bradykinin and measuring the accumulation of inositol phosphates ($IP_1$, $IP_2$, and $IP_3$).

With minor modifications, the method was based on techniques previously described by Steinberg S. F., and Alter A. in a study on enhanced receptor-dependent inositol phosphate accumulation in hypoxic myocytes, in "Ann. J. Physiol." (1993) 265:H691–H698. Briefly, viable SMC ($2 \times 10^5$ cells/well) were seeded in 6 well culture plates (Corning, Staffordshire, UK), precoated with 25 ng/mm² fibronectin (Biological Industries, Beit Haemek, Israel) and incubated at 37° C. in 10% $CO_2$ in air with 5 μi/ml myo-[2-³H]inositol (NEN, Boston, Mass.) for 72 hours during which they reach confluency. After incubation, sonication was performed according to protocol and the SMC washed with HEPES-buffered saline (pH 7.4) and incubated at room temperature for 2 hours with DMEM containing 10 mM LiCl (Sigma, St. Louis, Mo.). Experiments were conducted 2 hours after sonication, using $10^{-6}$M bradykinin stimulation (Sigma, St. Louis, Mo.), for 2 minutes. An experiment was terminated by the addition of ice-cold methanol, lipids were extracted, phases separated and the inositol phosphates in the aqueous phase fractionated by Dowex anion chromatography (Bio-Rad, Richmond, Calif.). Radiolabeled IP samples after fractionation were analyzed (10 ml scintillation liquid/vial: Quicksafe A, Zinsser, Germany) in a liquid scintillation analyzer (1600 TR, Packard, Conn.), and the separation of inositol mono ($IP_1$), di ($IP_2$) and tri ($IP_3$) phosphates verified using standards of tritiated inositol phosphates. Bradykinin-stimulated and non-stimulated SMC were studied. Bradykinin-stimulation was expressed as fold stimulation: the ratio of the mean CPM of stimulated SMC to the mean of non-stimulated cells. Non-sonicated SMC served as controls.

SMC were cultured in 24-well culture dishes and sonication performed before full confluence of the cultures. Ten minutes after sonication, the cultures were washed gently with PBS, fixed in situ with 2.5% glutaraldehyde and 2% paraformaldehyde in PBS for 2 hours at 4° C. The fixed cells were washed in PBS, post-fixed with 1% osmium tetroxide in 0.1 mole/L cacodylate buffer (pH 7.3) and dehydrated through a graded ethanol series. Cells were dried with liquid $CO_2$ at the critical point, coated with gold by sputtering in a vacuum evaporator. The morphology of two hundred cells was studied by scanning electron microscope (Jeol SEM 840, Tokyo, Japan).

Sonication did not effect inositol phosphate accumulation, as measured by activation of the α-adrenergic receptor-PLC pathway by triggering the α-adrenergic receptor with bradykinin. No change in the basal accumulation was apparent. The accumulation of inositol phosphates of sonicated SMC did not differ from that of non-sonicated cells 2 hours after sonication. The quantitative increases of inositol phosphates of bradykinin-stimulated cells after 2 minutes of stimulation, were similar to those of the ultrasound-treated and the control groups: $IP_1$=1.44±0.2 vs. 1.42±0.2 fold, p=NS; $IP_2$=1.79±0.15 vs. 1.8±0.14 fold, p=NS; $IP_3$=1.52±0.2 vs. 1.44±0.2 fold, p=NS.

In summary, therapeutic ULS causes structural changes in SMC cytoskeleton, which create the basis for the altered morphology and function of SMC.

From a therapeutic point of view, a useful strategy is one which is targeted at disrupting the migration apparatus (i.e. cytoskeleton), thus leading to arrest of migration and adherence of SMC after arterial injury. Three biological functions have been identified by Casscells W., in a study on migration of smooth muscle and endothelial cells reported in "Circulation" (1992) 86:723–729 as essential for the migration of SMC. They are: release of proteolytic agents, adherence to extracellular matrix, and the chemotactic response. The data presented herein suggests the unexpected results that ULS can inhibit the latter two of these SMC functions by virtue of its selective damage to actin fibers and the changes it effects on focal adhesion.

Although the above description relates to a specific ultrasonic energy level, the invention is not restricted to the specific level or frequency exemplified. In general, the energy level is dependent on the power being above the cavitation threshold of water.

Figure 8:
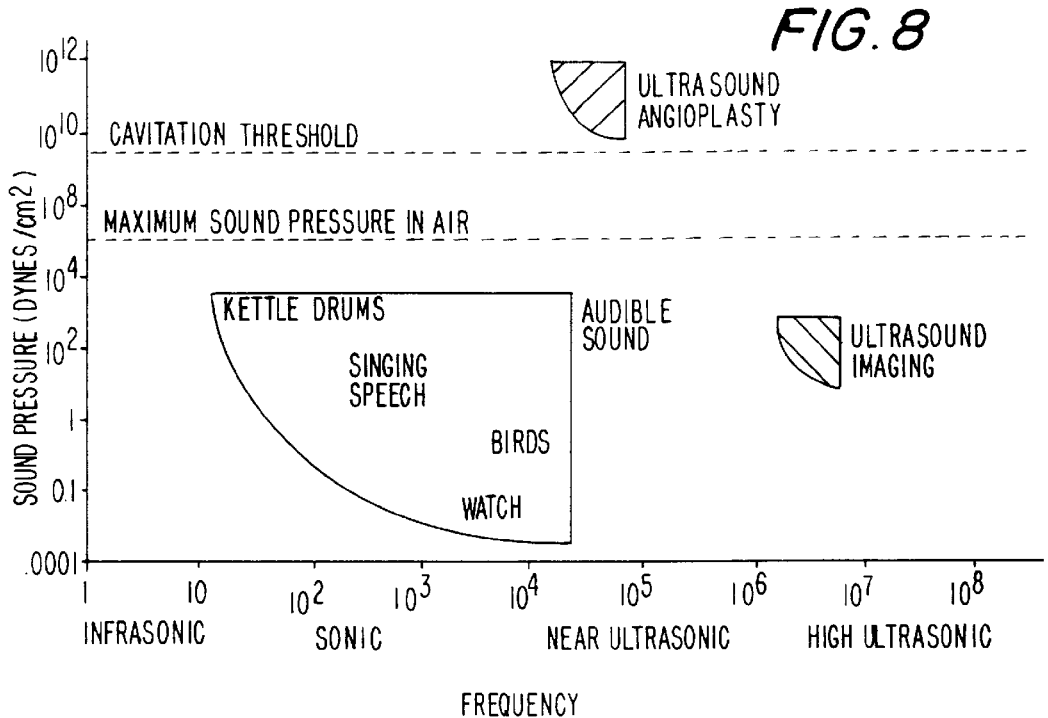
FIG. 8 is a graphic representation of the spectrum of sound. Frequency (in kHz) is displayed on the X axis and intensity (in Dynes/cm$^2$) on the Y axis.

With respect to the frequency, FIG. 8 roughly illustrates the frequency location of several acoustic phenomena. In ultrasound thrombolysis, frequencies at the lower end of ultrasound (20–40 kHz, with high intensities) are employed. In ultrasound imaging, higher frequencies, in the megahertz range, and low intensities are employed. Still, the cavitation effect will be present with any ultrasound frequency in intensities above the maximum sound pressure in water (the cavitation threshold). In general, the lowest possible frequency will be chosen, depending on system-dependent limitations (e.g. length of probe, invasive vs. non-invasive method, etc.). Preferably, the frequency will be in the range of 15–250 kHz.

To compensate for multiple-variable changes in the cavitation threshold, it is desirable to choose the power level with the help of an ultrasound imaging system such as described by Rosenschein U., Rozenszsajn L. A., Kraus L., Maraboe C. C., Walkins J. F., Rose E. A., Cannon J. P., and Weinstein J. S. in their work on ultrasonic angioplasty in totally occluded peripheral arteries reported in "Circulation" (1991) 83:1976–1986. Thus, the area to be treated is imaged by ULS while the power level is progressively increased. When the cavitation threshold is reached, microbubbles appear on the ULS-imaging screen. This will be the preferable power level and frequency to be used for treating the target area. Thus, the doctor or clinician can customize the optimal ULS dose level for each condition.

An especially important aspect of the method of the invention is in the prevention of restenosis in a blood vessel of a mammal following angioplasty. As stated above, restenosis is associated with the migration of SMC in the blood vessel. By reducing or inhibiting migration of SMC as a result of the ULS treatment described herein, the likelihood of restenosis occurring following vascular intervention is decreased.

The therapeutic use of ULS for recanalization of occluded arteries has been described in the literature. The use of ULS for the prophylaxis of restenosis following angioplasty would typically be done subsequent to such procedure. The ultrasonic energy may be transmitted to the occluded or stenotic artery either directly by the insertion of an ultrasonic probe into the blood vessel, or in a non-invasive manner. The following non-limiting examples illustrate certain therapeutic methods in accordance with the invention.

Embodiment 1: Invasive Ultrasonic Treatment

Figure 9:
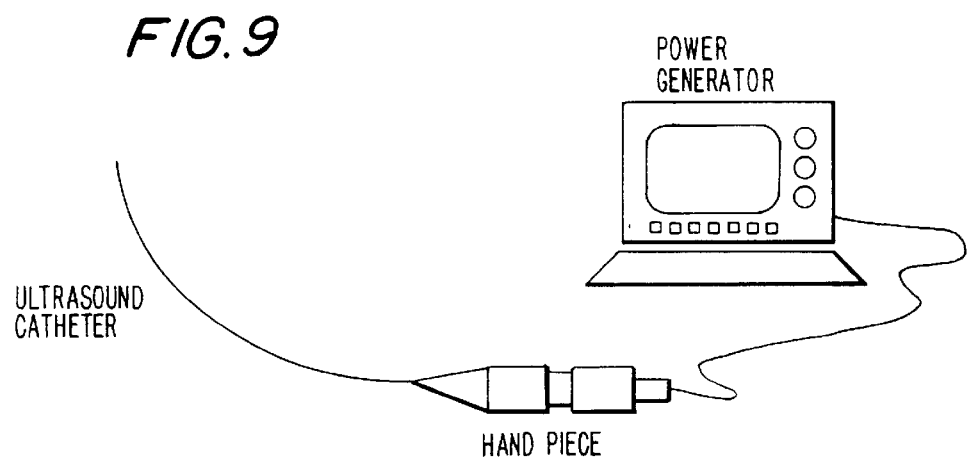
FIG. 9 is a schematic illustration of an invasive ultrasonic device in accordance with one embodiment of the system of the invention.

An invasive ultrasonic device would be composed of the following elements shown in the embodiment of FIG. 9. A power generator 20, supplies the restenosis inhibiting system 10 with the electrical energy needed to produce ultrasonic energy. An ultrasound transducer 30 in the handpiece 40, consists of piezoelectric elements (not shown) that convert electrical energy into ultrasonic energy. An ultrasonic transmission wire 50 is connected at its proximal end to the transducer and has an ultrasound tip 60 at the other end. The ultrasonic energy is transmitted as a longitudinal vibration of transmission wire 50 which thereby directs ultrasound energy into the arterial system of a patient (not shown).

The frequency level of ultrasound energy used is typically 20 kHz in vitro, in vivo and in human peripheral arterial studies, and 45 kHz in coronary artery studies.

Power is supplied by power generator 20. Peripheral arterial studies were performed with a power, for example, of about 20±2 W in vivo, and of about 12.0±0.9 W in humans. Coronary arterial studies are typically carried out with a power of about 18±2 W. System power is translated into longitudinal displacement of ultrasound tip 60, measuring 150±25 $\mu$m in initial studies and 10–15 $\mu$m in coronary artery application. The change of amplitude in coronary artery application resulted from the selection of thrombus, rather than atherosclerotic plaque, as the principal target of ablation in coronary arteries as the therapeutic target.

The exact operating parameters will be determined depending on the specific ultrasound system being used as well as on the target tissue. A doctor or clinician of ordinary skill in the art will know how to determine the optimal parameters.

Embodiment 2: Non-invasive Ultrasonic Treatment

Non-invasive ultrasound technology enables delivery of ultrasonic energy from a source outside the human body to a specific internal location. The intensity level of the energy in the treatment has to be high enough to create acoustic transient cavitation at the locus of therapy.

In order to eliminate any risk in that respect, the energy is preferably transmitted to the treatment area in such a way that the energy is focused only at the target location. Being unfocused along the way, minimal heat is created and no risk is involved. Either continuous wave or pulsed wave ULS can be used.

The device can be made compatible with ultrasound imaging systems by the addition of a dedicated therapeutic ultrasound probe. The combined system can serve as both an imaging probe and a treatment probe, thereby transmitting the required ablating energy to the selected target under ultrasound imaging. A software package can add the capability to support the visualization of the target, and the activation of the therapeutic energy transmission at the target.

The operation and handling of the device will also be similar to ultrasound imaging systems, with the addition of activation of non-invasive therapeutic ultrasound transmission.

A system for the prevention of restenosis in a blood vessel of a mammal following angioplasty in accordance with the present invention may typically include a therapeutic ultrasound probe, preferably containing therapeutic and imaging capabilities. The therapeutic ultrasound element can be based on any method for focusing ultrasound (e.g., geometric, annular array, phase array). The system will typically also include a control unit for controlling the ultrasonic energy output, which may preferably include a monitor, similar to regular imaging monitors, and more preferably, along with the software and hardware, suitable for operating the combined imaging and therapeutic transducer.

Clinical Experiments

Patients with anterior acute myocardial infarction were considered for the study. Patients were determined to be eligible if they showed evidence of anterior AMI defined by ischemic chest pain for <12 hours, accompanied by ST elevation $\geq 1$ mm in $\geq 2$ precordial leads. On angiography, there was thrombolysis in myocardial infarction (TIMI) grade flow 0 or 1 in the left anterior descending artery (LAD).

An ultrasound thrombolysis device (Angiosonics Inc.) is a 140-cm long solid aluminum alloy probe, ensheathed in a plastic catheter and connected at its proximal end to a piezoelectric transducer. Ultrasonic energy is transmitted from the transducer as longitudinal vibrations of the probe which directs the energy into the arterial system. The last 18 cm of the device is a three-wire flexible segment with a 1.6 mm tip designed to optimize the thrombolytic effect of the ultrasound energy. The three wire flexible segment permits the use of a solid metal transmitter for optimal ultrasound transmission, while remaining flexible.

Power output at the handpiece was controlled by an integrated computer designed to ensure constant output at the distal tip under variable loading conditions encountered during the procedure, and was set at about 18 watts.

The ultrasound probe was attached to a guidewire and advanced into the LAD under flouroscopy until the cavitation tip was positioned between about 1 to 2 mm past the proximal end of the occlusion. Sonication (at 18 watts) was carried out to ablate the clot. Therapeutic ultrasound induced normalization of perfusion, and a TIMI grade 3 was achieved with no adverse angiographic signs. At the end of the procedure, the probe was then used to irradiate the vascular intima over the length of the stenosis, thereby inhibiting the migration, viability and adherance of the smooth muscle cells in the lumen. Then, at a six-month follow up, seven of the 14 patients studied underwent intravascular ultrasound (IVUS) of the sonicated arterial segment. In six patients, IVUS has shown minimal myo-intimal proliferation and in only one patient was any significant myo-intimal growth accompanied by lumen narrowing observed. This data suggest the unexpected benefit that therapeutic ultrasound in accordance with the present invention is effective in preventing restinosis following vascular intervention.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed:

1. A method of inhibiting restenosis in mammals, comprising:
   treating a stenosis of a blood vessel of a mammal, said treatment causing injury to the vessel wall in the region of the stenosis;
   applying ultrasound within the vessel to cause cavitation within the vessel in the region of the injury and irradiating smooth muscle cells in the region of the injury with sufficient ultrasound energy to reduce the migration capacity of the smooth muscle cells at least about 2.4 fold without the use of restenosis inhibiting drugs.

2. The method of inhibiting restenosis in mammals of claim 1, wherein said ultrasonic energy supplied is above at least 22.5 watt·sec and the cavitation threshold of blood.

3. The method of inhibiting restenosis in mammals of claim 1, wherein said ultrasonic energy has a frequency in the range of about 1 kHz. to about 3 MHz.

4. The method of inhibiting restenosis in mammals of claim 1, wherein said ultrasonic energy has a frequency in the range of about 15 kHz. to about 250 kHz.

5. The method of inhibiting restenosis in mammals of claim 1, wherein said irradiating mammalian smooth muscle cells with a restenosis-inhibiting amount of ultrasonic energy occurs after a cardiovascular therapy.

6. The method inhibiting restenosis in mammals of claim 5, wherein said cardiovascular therapy is balloon angioplasty.

7. A therapeutic method for the prevention of restenosis associated with smooth muscle cell migration and adherence in a blood vessel of a mammal following vascular intervention, comprising:
   exposing smooth muscle cells in a blood vessel to sufficient ultrasonic energy to reduce the migration capacity of the smooth muscle cells without the use of restenosis inhibiting drugs, at least about 2.4 fold.

8. The therapeutic method for the prevention of restenosis associated with smooth muscle cell migration and adherence in a blood vessel of a mammal following vascular intervention of claim 7, wherein said blood vessel is exposed to said ultrasonic energy by insertion of an ultrasound probe into said blood vessel which causes cavitation within the vessel.

9. The method of claim 8, wherein said ultrasonic energy supplied is above about 22.5 watt·sec and the cavitation threshold of blood.

10. The method of claim 8, wherein said ultrasonic energy has a frequency in the range of about 1 kHz to about 3 MHz.

11. The method of claim 8, wherein said vascular intervention is balloon angioplasty.

12. The therapeutic method for the prevention of restenosis associated with smooth muscle cell migration and adherence in a blood vessel of a mammal following vascular intervention of claim 7, wherein said blood vessel is exposed to said ultrasonic energy in a non-invasive manner.

13. The therapeutic method for the prevention of restenosis associated with smooth muscle cell migration and adherence in a blood vessel of a mammal following vascular intervention of claim 7, wherein said exposing smooth muscle cells in a blood vessel to ultrasonic energy occurs after a cardiovascular therapy.

14. The therapeutic method for the prevention of restenosis associated with smooth muscle cell migration and adherence in a blood vessel of a mammal following vascular intervention of claim 13, wherein said cardiovascular therapy is one of balloon angioplasty, endarterectomy laser drills, stents, thermal fusion, mechanical drills, and arthrectomy.

15. The method of claim 1, wherein ultrasound is applied with an ultrasonic energy source for providing ultrasonic energy; a transmitter for transmitting said ultrasonic energy to a blood vessel; and a control unit controlling said ultrasonic energy source, said ultrasonic energy source, said transmitter and said control unit being constructed and arranged to transmit said ultrasonic energy to said blood vessel in a restenosis inhibiting amount to compromise the migration of smooth muscle cells contained in said blood vessel.

16. The method of claim 1, wherein the treatment includes the implantation of a stent.

* * * * *